United States Patent [19]

Sado et al.

[11] 4,342,723
[45] Aug. 3, 1982

[54] GAS-EXCHANGE SHEET MEMBERS

[75] Inventors: Ryoichi Sado, Saitama; Kazutoki Tahara, Ageo, both of Japan

[73] Assignee: Shin-Etsu Polymer Co., Ltd., Japan

[21] Appl. No.: 165,729

[22] Filed: Jul. 3, 1980

Related U.S. Application Data

[63] Continuation-in-part of Ser. No. 96,567, Nov. 21, 1979, abandoned.

[30] Foreign Application Priority Data

Nov. 24, 1978 [JP] Japan .................................. 53-145171
Dec. 30, 1978 [JP] Japan .................................. 53-165825

[51] Int. Cl.$^3$ .............................................. B01D 31/00
[52] U.S. Cl. .................................. 422/48; 55/158; 210/321.4
[58] Field of Search ............... 210/323 R, 22 A, 22 C, 210/22 D, 321 A, 321 B, 321 R, 346, 500 M; 422/48; 55/16, 158; 128/1 D

[56] References Cited

U.S. PATENT DOCUMENTS

| | | | |
|---|---|---|---|
| 3,228,877 | 1/1966 | Mahon ................................. | 210/22 |
| 3,522,885 | 8/1970 | Lavender et al. ................. | 210/321 B |
| 3,724,673 | 4/1973 | Ryon .................................. | 422/48 X |
| 4,176,069 | 11/1979 | Metz et al. ........................ | 422/48 X |

FOREIGN PATENT DOCUMENTS 2523236 12/1975 Fed. Rep. of Germany ... 210/321 B

*Primary Examiner*—Frank A. Spear, Jr.
*Attorney, Agent, or Firm*—Hill, Van Santen, Steadman, Chiara & Simpson

[57] ABSTRACT

A sheet member of silicone rubber suitable for use in gas-exchange such as oxygenation and decarbonation of blood in an oxygenator of a mechanical heart and lung is proposed.

The sheet member of the invention is provided with a plurality of capillary pores extending in parallel and each opening at both ends thereof. The oxygenator is constructed with a plurality of the inventive sheet members arranged in parallel and air is passed through the spaces between the adjacent sheet members while blood is passed through the capillary pores in the sheet members.

The efficiency of the gas exchange by use of the above sheet members is further enhanced by providing the sheet member with capillary pores each having an undulating longitudinal cross section comprised of an alternating repetition of wider portions and narrower portions.

7 Claims, 14 Drawing Figures

FIG. 8
FIG. 9
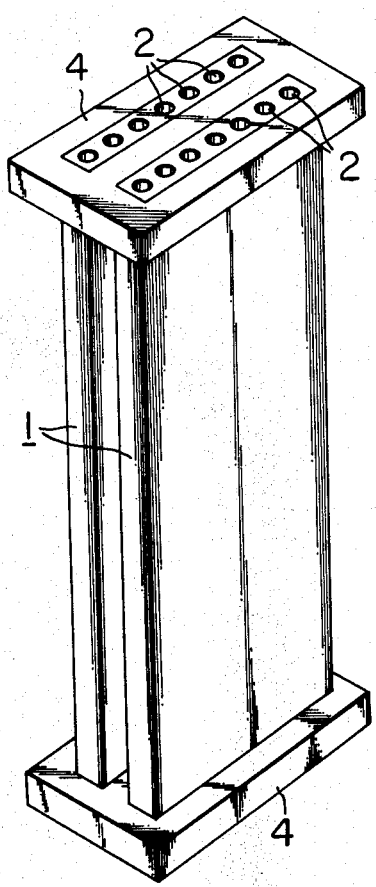
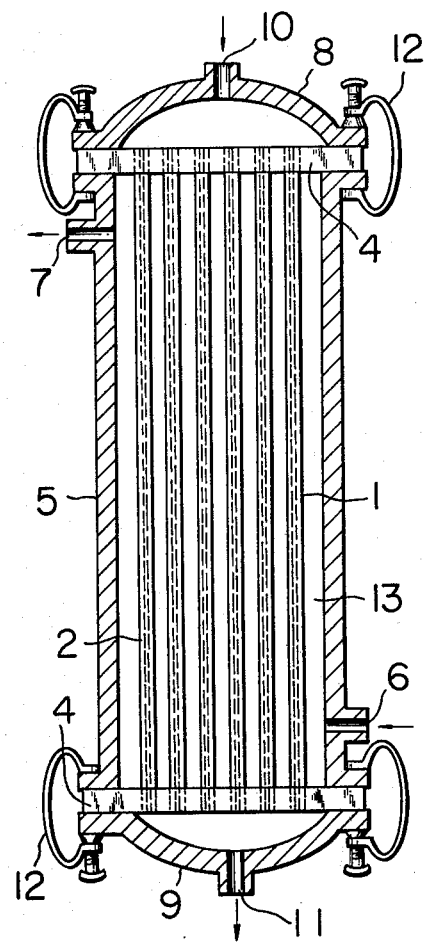

4,342,723

GAS-EXCHANGE SHEET MEMBERS

BACKGROUND OF THE INVENTION

This is a continuation-in-part application of a U.S. patent application Ser. No. 96,567 filed Nov. 21, 1979, now abandoned.

The present invention relates to a sheet member used for gas-exchange between two different fluids or, in particular, to a sheet member useful for the gas-exchange between a gaseous phase and a liquid phase as in the oxygenetors in a mechanical heart and lung.

With the development of the medical science, as is well known, many of the surgical operations are performed with the aid of a mechanical heart and lung having an oxygenator in which the blood of the patient is decarbonated and oxygenated to be returned to the patient's body. In the early days of the use of the mechanical heart and lung, the gas-exchange in oxygenators was dependent on the principle of direct contact between blood and air. Due to the drawbacks such as hemolysis and denaturation of the proteins in the blood plasma, oxygenators of the direct-contact type have been replaced with oxygenators of gas-permeable membrane type in which blood and air are brought into indirect contact through a membrane having permeability for oxygen and carbon dioxide.

Among many properties essential in the material of the gas-exchange membranes in such an oxygenator, the permeability of the gases is of course the most important and, in this connection, silicone rubbers are recommended owing to their outstandingly large permeability coefficients for oxygen and carbon dioxide.

The conventional membrane-type oxygenators can be classified into two types according to their structures. The first is the so-called plain-film type in which a plurality of thin sheets or films of a silicone rubber are mounted in parallel with narrow spaces between adjacent ones being provided by the use of suitable spacers. Blood and air are passed in these spaces in such a manner that each of the sheets or films is in simultaneous contact with the blood on one side and with air on the other side thereof and decarbonation and oxygenation are effected through the sheet or film.

The other class of the membrane-type oxygenators is the capillary type in which a plurality of thin-wall capillary tubes of a silicone rubber are bundled together. The air is passed around the bundle while the blood is passed through the capillary tubes or vice versa.

The above described prior art oxygenators have their own defects. For example, the plain-film types are disadvantageous due to the difficulty in the efficient detection of pin holes which necessitates much labor and in addition the plain films are susceptible to scratches which lead to the formation of pin holes or tears. Furthermore, difficulties are encountered in assembling these plain films into a unit for the oxygenator by mounting the films on frames with narrow spaces therebetween. Capillary-tube oxygenators are, on the other hand, defective because thin-wall capillaries are readily collapsed by an external pressure and become deformed to cause possible blocking of the tubes. In addition, the utilizable surface area of the bundled capillary tubes is somewhat reduced since the surface portion of the capillary tubes in contact with the other capillary tubes cannot be contacted by the air.

SUMMARY OF THE INVENTION

Thus, it is an object of the present invention to provide a novel sheet member with which gas-exchange between a liquid, e.g. blood, and a gas, e.g. air, as in an oxygenator of a mechanical heart and lung, can be effected with high efficiency and is capable of providing an oxygenator free from the above described problems of the prior art oxygenators.

The gas-exchange sheet member of the present invention is made of a silicone rubber and is provided with a plurality of capillary pores extending in aligned substantially parallel relation with each other and each pore opening at both ends thereof.

A further preferred embodiment concerns an inventive gas-exchange sheet member which has capillaries each having an undulating longitudinal cross section and with each capillary being composed of an alternating repetition of wider portions and narrower portions.

BRIEF DESCRIPTION OF THE DRAWING

FIG. 8 is a perspective view of two sheet members mounted on two common flanges.

FIG. 9 is an axial cross sectional view of an oxygenator constructed with the inventive sheet members.

DETAILED DESCRIPTION OF THE PREFERRED EMBODIMENTS

The gas-exchange sheet member of the invention is now described with reference to the annexed drawings.

Figure 1:
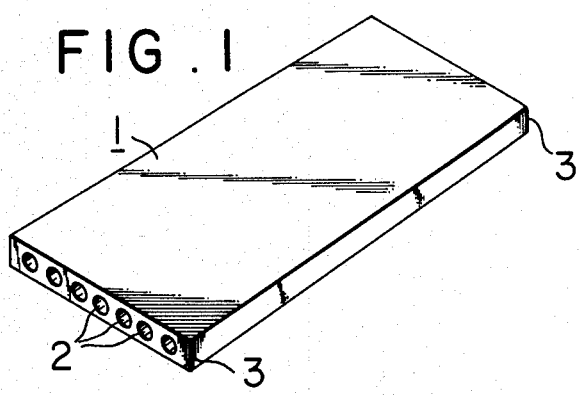
FIG. 1 is a perspective view of an inventive sheet member provided with capillary pores of a circular cross section.
Figure 2:
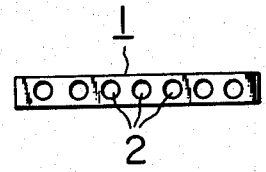
FIG. 2 is a cross sectional view of the sheet member of FIG. 1 as cut in the plane perpendicular to the direction of the capillary pores.

In FIG. 1 a gas-exchange sheet member is illustrated according to the invention. The sheet member 1 is preferably comprised of a silicone rubber and is shaped preferably in the form of a rectangle and is provided with a plurality of capillary pores 2 extending in straight lines in the direction of the longer side of the rectangular sheet 1. The capillary pores 2 run within the sheet 1 substantially in parallel with each other and each of the ends of the capillary pores 2 opens at the respective end surfaces 3 of the sheet member 1. As is shown in the end surface 3 of the sheet 1, the cross sections of the capillary pores 2 are arranged within the cross section of the sheet member 1 in a row with, preferably, regular intervals or spacings as is shown in FIG. 2. FIG. 2 illustrates a cross section of the sheet member 1.

Figure 3:
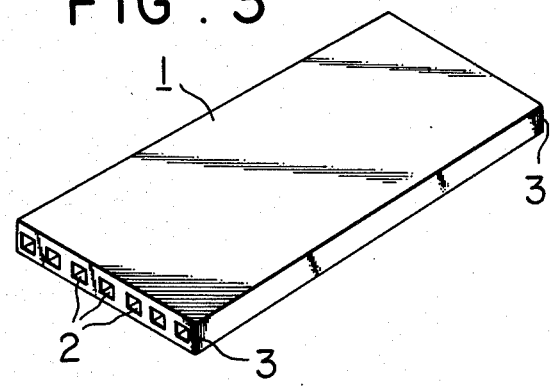
FIG. 3 is a perspective view of an inventive sheet member provided with capillary pores of a rectangular cross section.
Figure 4:
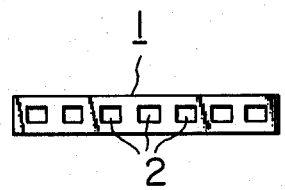
FIG. 4 is a cross sectional view of the sheet member of FIG. 3 as cut in the plane perpendicular to the direction of the capillary pores.
Figure 5:
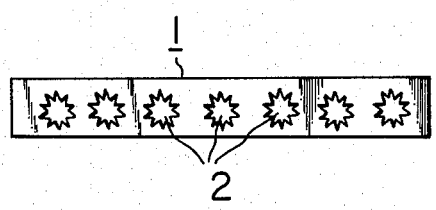
FIG. 5 is a cross sectional view of another embodiment of the inventive sheet member provided with capillary pores of irregular cross sections.

The cross section of the capillary pores 2 is not limited to being circular as is shown in FIG. 1 and FIG. 2 but it may be square or rectangular as is shown in FIG. 3 and FIG. 4. FIGS. 3 and 4 illustrate another embodiment of the sheet member 1. It is sometimes advantageous that the capillary pores 2 have irregular cross sectional forms (FIG. 5) so that the effective surface area of the capillary pores can be increased.

It is optional that each of the capillary pores 2 meanders within the sheet member 1 instead of extending in a straight line as stated before.

Assuming that the cross section of the capillary pores 2 is circular as is shown in FIG. 1 and FIG. 2, the diameter of the capillary pores 2 is preferably in the range from 0.02 to 3 mm or, more preferably, from 0.15 to 0.5 mm in consideration of the balance of the effective surface area and the pressure head of the blood flowing in the capillary pores 2. When the diameter of the capillary pores 2 is smaller than stated above, the resistance against blood flow in the capillary pores 2 is unduly increased thus resulting in the possible destruction of the blood cells though with correspondingly increased surface area leading to the consequent decrease in the overall efficiency of gas exchange. Where the pores 2 have diameters larger than 3 mm the disadvantageous are due to the decreased surface area per unit area of the cross section of the capillary pores 2 so that the compactness of the oxygenator as a whole is reduced.

The distance between two adjacent capillary pores 2 is desirably as small as possible so that sufficient mechanical strengths can be ensured in the sheet member 1 as a whole and so that the overall cross sectional area of the capillary pores 2 in a sheet member 1 is maximized. On the other hand, the wall thickness of the capillary pores 2 in the direction toward the surface of the sheet member 1 is preferably in the range from 0.03 mm to 0.3 mm. When this wall thickness is smaller than 0.03 mm, there may be dangers that pin holes are formed in the pore walls to cause fatal drawbacks in the use of the sheet member 1 in an oxygenator and also that either the sheet member 1 itself is expanded with increased pressure of the blood flowing in the capillary pores 2 with eventual bursting of the sheet member 1, or the capillary pores are collapsed, when the pressure of the air is excessively increased, to cause the interruption of the blood flow in the capillary pores. A larger thickness of the walls of the capillary pores 2, which thickness is larger than 0.3 mm, is, of course, undesirable due to the decreased efficiency of the gas exchange through the walls.

Figure 6:
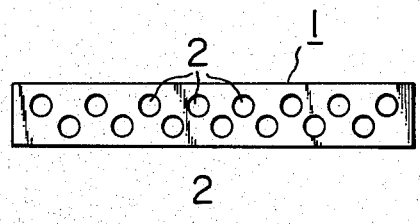
FIG. 6 is a cross sectional view of a sheet member provided with capillary pores arranged in two rows.
Figure 7:
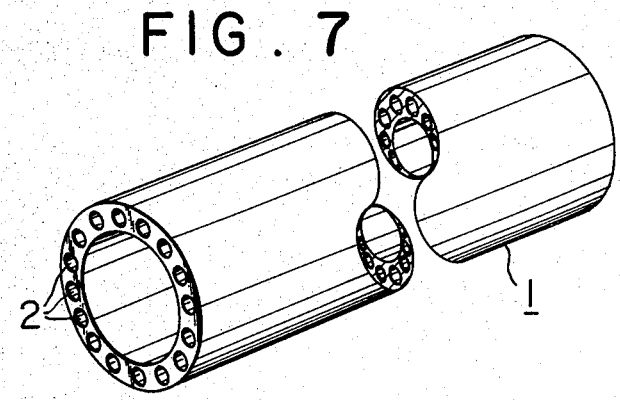
FIG. 7 is a perspective view of a cylindrical modification of the inventive sheet member.

It is optional that the capillary pores 2 are arranged in two rows or more in the cross section as is shown in FIG. 6 so that the mechanical strength of the sheet member 1 is increased without substantial loss in the efficiency of the gas exchange. Further, the sheet member 1 according to need may be either in the form of a plain sheet as is shown in FIGS. 1 and 3 or in the form of a cylinder as is shown in FIG. 7.

The sheet member 1 is prepared in the following manner. Thus, a plurality of wires or strings which are arranged in parallel are embedded in a sheet of an uncured silicone rubber stock which is subsequently subjected to curing into a rubbery elastomer. Then the wires or strings are pulled out of the cured silicone rubber sheet.

A convenient way for assembling the sheet members 1 into an oxygenator is that each of the sheet members 1 is provided at both ends thereof with respective flanges 4 or that two or more of the sheet members 1 are provided with common flanges 4 on both of their ends by adhesive bonding as is shown in FIG. 8.

FIG. 9 illustrates an axial cross sectional view of an example of the oxygenator constructed by use of the inventive gas-exchange sheet members 1. Six of the members 1 are mounted on two common flanges 4,4 which are also made of a silicone rubber. The flanged assembly of the sheet members 1 is placed inside a body 5 of the oxygenator. The body 5 is provided with an air inlet 6 and an air outlet 7 at positions near the different ends thereof. Each of the flanges 4,4 is covered by an end plate 8 or 9 provided with a blood inlet 10 or blood outlet 11. The end plates 8 and 9 are fastened to the body 5 of the oxygenator by means of a plurality of clamps 12. The flanges 4,4 serve as the gaskets therebetween so that the air chamber 13 inside the body 5 of the oxygenator is hermetically sealed to ensure that the air in the air chamber 13 only has indirect contact with the blood flowing in the capillary pores 2 through the walls of the capillary pores 2. In this arrangement of the sheet members 1 in the oxygenator, it is recommended that the distance between adjacent sheet members 1 be as small as possible so that the whole assembly can be constructed with compactness. In this connection, it is usual that the sheet members 1 are stretched between the ends of the body 5 of the oxygenator under a small tension so that each of the sheet members 1 lies in a plane with good parallelism with neighboring sheet members although it is optional to have the sheet members 1 loosely received in the body 5. It is sometimes advantageous that the air flowing in the air chamber 13 is pressurized to the maximum amount that the capillary pores 2 of the sheet members can withstand so that the efficiency of the oxygen permeation through the walls of the capillary pores 2 can be increased.

Figure 10:
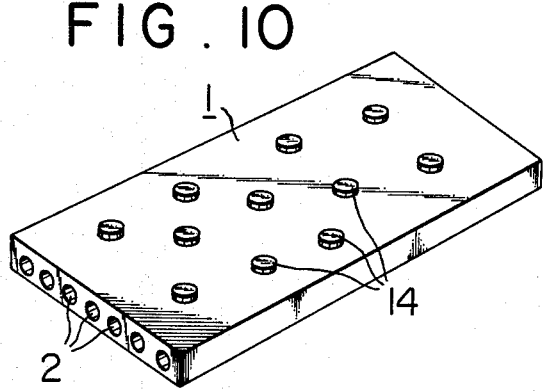
FIGS. 10 and 11 are perspective views of the inventive sheet members provided with protrusions on surfaces thereof distributed at random thereon.
Figure 11:
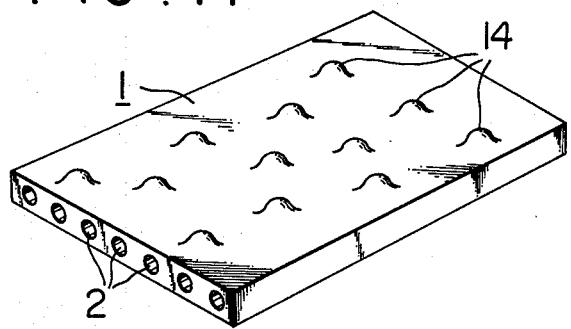

It is noteworthy that the adjacent sheet members 1 may sometimes stick to each other to hinder the smooth flow of the air in the spaces between them when the distance between two adjacent sheet members 1 is minimized with the above described object of obtaining compactness of the apparatus. In this connection, an improvement is made on the surface condition of at least one side of each of the sheet members 1. A plurality of stud-like or smoothly raised protrusions 14 are provided at random on the surface of the sheet member 1 as is shown in FIG. 10 and FIG. 11. When provided with these protrusions 14, the sheet members 1 never stick and adhere to the neighboring ones even when the sheet members are mounted on flanges with the closest distance between each other. An additional advantage is obtained by providing these protrusions 14 on the surface of the sheet members 1 whereby the flow of the blood in the capillary pores 2 of the sheet members 1 is made turbulent. The turbulence occurs as a result of a deformation of the capillary pores 2 owing to the presence of the protrusions 14 when the sheet members 1 are mounted in direct contact with each other. The thus created turbulence is a very important condition for enhancing the efficiency of the gas exchange between the air flowing along the surface of the sheet members 1 and the blood passing through the capillary pores 2 in the sheet members 1.

Figure 12A:
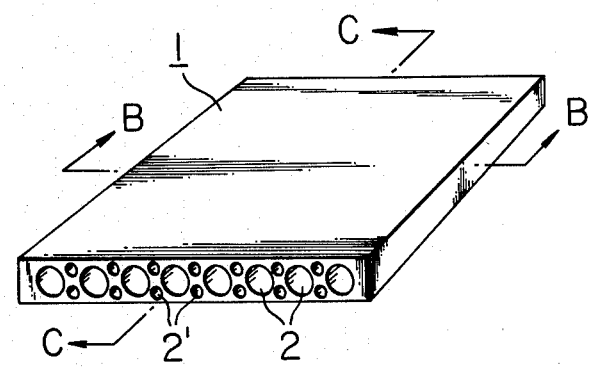
FIGS. 12A, 12B and 12C constitute a perspective view, a transverse cross sectional view and a longitudinal cross sectional view of an inventive sheet member having undulating capillaries.
Figure 12B:
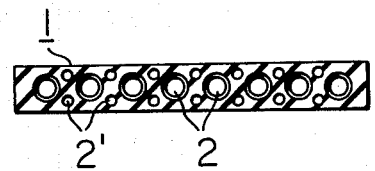
Figure 12C:
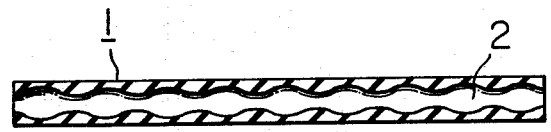

A further preferred embodiment of the inventive gas-exchange sheet member is illustrated in FIGS. 12A to 12C. The sheet member 1 illustrated there has capillary pores 2,2 each with an undulating longitudinal cross section as shown in FIG. 12C. FIG. 12C is a cross sectional view taken along the line C—C in FIG. 12A. That is to say, each of the capillary pores is composed of an alternate repetition of wider portions and narrower portions. With this capillary configuration, growth of a laminar boundary layer of liquid flow is most effectively prevented and the fluid, e.g. blood, passing through the capillary pore flows turbulently so that the efficiency in the gas exchange can be remarkably improved.

In order that the above mentioned turbulent flow can be fully exhibited, it is necessary that the difference between the diameters of the wider portions and the narrower portions is in the range from 10 to 400 μm and the pitch of the undulation is in the range from 30 to 100 μm. The reason for these dimensional limitations is that a smaller difference in diameters and a larger pitch of the undulation than the above given ranges do not prevent the growth of laminar flow while a larger difference in diameters and a smaller pitch of undulation are dangerous because of possible increase of thrombus of the blood. For avoiding thrombus, it is desirable that the diameter of the capillary along its length exhibits a smooth and gradual transition from a wider portion to a narrower portion thus prohibiting the formation of any dead space in the capillary pore.

The sheet members having undulating capillary pores can be readily prepared in several ways. For example, a curable silicone rubber composition having flowability is cast into a mold in which a plurality of mandrel wires having an undulating diameter corresponding to the desired capillary pores are placed under tension. The composition of the silicone rubber is then cured. The mandrel wires are pulled out of the cured composition. No difficulties are usually encountered in pulling out the undulating mandrel wires when the surface of the wires have been treated in advance with a suitable releasing agent. If difficulties are still encountered in pulling out the undulating mandrel wires despite the use of a releasing agent, the cured silicone rubber can be swelled with a suitable organic solvent so that the wires can be readily pulled out from the swollen rubber. The swollen rubber can then be subsequently dried by the evaporation of the solvent to cause it to regain its original dimensions. The removal of the undulating mandrel wires also can be carried out by dissolving or decomposing away the wires when the wires are made of a material susceptible to dissolution or decomposition. Wires of this type can be dissolved by means of heat or by means of suitable solvents or chemicals.

A further alternative for forming a sheet having undulating pores is obtained by an extrusion molding process in which the velocity of extrusion is pulsatingly controlled by use of a limiting former for controlling the outer dimensions of the sheet.

The sheet member 1, which is illustrated in FIGS. 12A to 12C, has capillaries composed of a set of capillary pores 2,2 having larger diameter and another set of capillary pores 2', 2' having a smaller diameter as is most clearly shown in FIG. 12B. FIG. 12B is a cross sectional view taken along the line B—B in FIG. 12A. With this arrangement of the capillary pores, the cross section of the sheet member 1 can be fully utilized giving a larger effective area for gas exchange.

What is claimed is:

1. A gas-exchange sheet member made of a silicone rubber and provided with a plurality of capillary pores extending in substantially aligned parallel relation with each other and each opening at opposite ends thereof, each of the capillary pores having an undulating longitudinal cross-section and being comprised of an alternate repetition of wider portions and narrower portions, and a plurality of protrusions being provided to extend from at least one surface of the sheet member and being positioned in random relation.

2. The sheet member as claimed in claim 1, wherein each of the capillary pores has an irregular cross section.

3. The sheet member as claimed in claim 1, wherein the difference in the diameters of the capillary pores between the wider portion and the narrower portion being in the range from 10 to 400 μm and the pitch of undulation being in the range from 30 to 100 μm.

4. The sheet member as claimed in claim 1, wherein the capillary pores are comprised of a first set of capillary pores and a second set of capillary pores each having a smaller diameter than the capillary pores belonging to the first set and the capillary pores of the second set being distributed between the capillary pores of the first set.

5. The member of claim 1 further characterized by each of said pores having a wall thickness in the range from 0.03 mm to 0.3 mm.

6. The member of claim 1 further characterized by the pores having a diameter preferably in the range from 0.15 to 0.5 mm.

7. An oxygenator in a mechanical heart and lung which comprises a tubular body having an air inlet and an air outlet, a plurality of sheet members made of a silicone rubber mounted in said body, a pair of support flanges made of silicone rubber and engaged with opposite ends of said sheet members maintaining the sheet members substantially in parallel relation with each other, each of the sheet members being provided with a plurality of capillary pores extending in substantially aligned parallel relation with each other through said support flanges and each of the capillary pores being open at opposite ends thereof and having an undulating longitudinal cross section and being comprised of an alternate repetition of wider portions and narrower portions, end plates positioned on opposite ends of the tubular body with one end plate having a blood inlet and with the other having a blood outlet to allow blood flow therethrough and also through said pores in said sheet member, and clamp means securing the outer margins of the end plates with opposite ends of said body and with said silicone rubber support flanges co-acting with the clamped outer margins of the end plates and the opposite ends of said body to provide hermetic seals when the clamping means is positioned in a clamped assembly.

* * * * *